(12) United States Patent
Petersen et al.

(10) Patent No.: US 6,509,483 B2
(45) Date of Patent: Jan. 21, 2003

(54) METHOD FOR THE PREPARATION OF CITALOPRAM

(75) Inventors: Hans Petersen, Vanløse (DK); Haleh Ahmadian, Solrød Strand (DK); Robert Dancer, Frederiksberg C (DK)

(73) Assignee: H. Lundbeck A/S, Valby-copenhagen (DK)

( * ) Notice: Subject to any disclaimer, the term of this patent is extended or adjusted under 35 U.S.C. 154(b) by 0 days.

(21) Appl. No.: 09/930,110

(22) Filed: Aug. 14, 2001

(65) Prior Publication Data

US 2002/0026062 A1 Feb. 28, 2002

(30) Foreign Application Priority Data

Aug. 18, 2000 (DK) .................................. 2000 01231

(51) Int. Cl.⁷ ............................................. C07D 307/87
(52) U.S. Cl. ..................................................... 549/467
(58) Field of Search ......................................... 549/467

(56) References Cited

U.S. PATENT DOCUMENTS

| | | | |
|---|---|---|---|
| 3,467,675 A | 9/1969 | Petersen et al. | 260/346.2 |
| 4,136,193 A * | 1/1979 | Bogeso | 549/467 |
| 4,650,884 A | 3/1987 | Bogeso | 549/467 |
| 4,943,590 A | 7/1990 | Boegesoe et al. | 415/469 |
| 5,296,507 A | 3/1994 | Tanaka et al. | 514/465 |
| 6,020,501 A | 2/2000 | Massonne et al. | 549/307 |
| 6,028,204 A | 2/2000 | Massonne et al. | 549/307 |
| 6,229,026 B1 | 5/2001 | Petersen | 549/467 |
| 6,258,842 B1 | 7/2001 | Petersen et al. | 514/469 |
| 6,291,689 B1 | 9/2001 | Petersen et al. | 549/467 |
| 6,310,222 B1 | 10/2001 | Ikemoto et al. | 549/467 |
| 6,365,747 B1 | 4/2002 | Dall'Asta et al. | 548/146 |
| 2001/0027256 A1 | 10/2001 | Petersen et al. | 549/462 |
| 2002/0004604 A1 | 1/2002 | Petersen et al. | 549/462 |
| 2002/0019546 A1 | 2/2002 | Petersen et al. | 549/307 |
| 2002/0025982 A1 | 2/2002 | Petersen et al. | 514/469 |
| 2002/0026062 A1 | 2/2002 | Petersen et al. | 549/467 |
| 2002/0028956 A1 | 3/2002 | Weber | 549/307 |
| 2002/0035277 A1 | 3/2002 | Rock et al. | 549/467 |
| 2002/0040153 A1 | 4/2002 | Petersen | 549/467 |

FOREIGN PATENT DOCUMENTS

| | | | |
|---|---|---|---|
| CA | 2023057 | 2/1991 | ......... C07C/211/08 |
| EP | 1 095 926 | 5/2001 | ........... C07C/33/46 |
| WO | 98/19511 | 5/1998 | |
| WO | 98/19512 | 5/1998 | |
| WO | 98/19513 | 5/1998 | |
| WO | 99/30548 | 6/1999 | |
| WO | 00/11926 | 3/2000 | |
| WO | 00/12044 | 3/2000 | |
| WO | 00/13648 | 3/2000 | |
| WO | 00/23431 | 4/2000 | ......... C07D/307/87 |
| WO | 00/39112 | 7/2000 | ......... C07D/307/87 |
| WO | 00/44738 | 8/2000 | ......... C07D/307/88 |
| WO | 01/45483 | 6/2001 | |
| WO | 01/47877 | 7/2001 | |
| WO | 01/66536 | 9/2001 | ......... C07D/307/87 |

OTHER PUBLICATIONS

U.S. patent application ser. No. 09/692,653, filed Oct. 19, 2000.
U.S. patent application ser. No. 10/012,025, filed Nov. 6, 2001.U.S. patent application ser. No. 10/012,054, filed Nov. 6, 2001.
U.S. patent application ser. No. 10/035,005, filed Dec. 20, 2001.
U.S. patent application ser. No. 10/046,126, filed Jan. 8, 2002.
Levy, L.F., "4–Aminophthalide and Some Derivatives", *J. Chem. Soc.* pp. 867–870 (1931).

(List continued on next page.)

*Primary Examiner*—Bernard Dentz
(74) *Attorney, Agent, or Firm*—Darby & Darby

(57) ABSTRACT

A method for the preparation of citalopram comprising reacting 5-carboxyphthalide successively with a Grignard reagent of 4-halo-fluorophenyl and a Grignard reagent of 3-halo-N,N-dimethyl-propylamine and then effecting ring closure of the resulting compound of Formula XI Formula XI

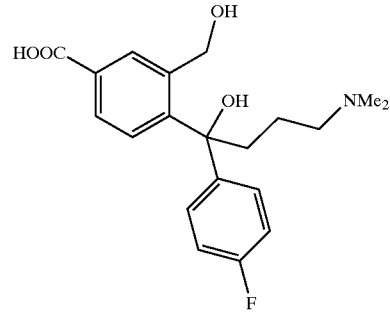

to a compound of Formula IV Formula IV

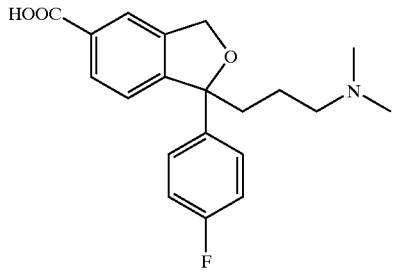

followed by conversion of the compound of Formula IV into citalopram is disclosed. Methods for the manufacture and conversion of the compound of Formula IV are also disclosed.

9 Claims, No Drawings

OTHER PUBLICATIONS

Tirouflet J., "Phtalide Substitutes en 5", *Bull. Soc. Sci. de Bretagne* 26:35–43 (1951).

Bigler, Allan et al., "Quantitative Structure–activity Relationships in a Series of Selective 5–HT uptake inhibitors," *Eur. J. Med. Chem.* 3:289–295 (1997).

Forney L., "Reaction of Terephthalic Acid with Formaldehyde in Sulfur Trioxide Media," *J. Org. Chem.* 35:1695–1696 (1970).

Dordor et al., "Reaction of Oxazolines with Phosphorous Oxychloride," *Tetrahedron Letters* 24:1437–1440 (1983).

Barton et al., *Comprehensive Organic Chemistry. The Synthesis and Reactions of Organic Compounds*, vol. 2, pp. 1024–1025.

Harrison, Ian T. et al., *Compenduim of Organic Synthetic Methods*, p. 458, John Wiley & Sons (New York: 1971).

* cited by examiner

METHOD FOR THE PREPARATION OF CITALOPRAM

The present invention relates to a method for the preparation of the well-known anti-depressant drug citalopram, 1-[3-(dimethylamino)propyl]-1-(4-fluorophenyl)-1,3-dihydro-5-isobenzofurancarbonitrile, methods for the preparation of intermediates used in the preparation of citalopram, and methods for conversion of said intermediates into citalopram.

BACKGROUND OF THE INVENTION

Citalopram is a well-known antidepressant drug that has now been on the market for some years and has the following structure:

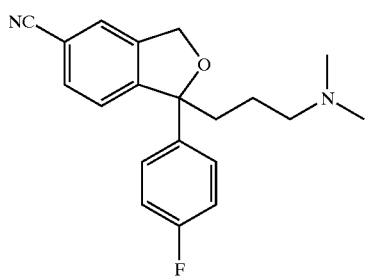

Formula I

It is a selective, centrally acting serotonin (5-hydroxytryptamine; 5-HT) reuptake inhibitor, accordingly having antidepressant activities. The antidepressant activity of the compound has been reported in several publications, eg. J. Hyttel *Prog. Neuro-Psychopharmacol. & Biol. Psychiat.* 1982, 6, 277–295 and A. Gravem *Acta Psychiatr. Scand.* 1987, 75, 478–486. The compound has further been disclosed to show effects in the treatment of dementia and cerebrovascular disorders, EP-A 474580.

Citalopram was first disclosed in DE 2,657,013, corresponding to U.S. Pat. No. 4,136,193. This patent publication describes the preparation of citalopram by one method and outlines a further method which may be used for preparing citalopram.

According to the process described, the corresponding 1-(4-fluorophenyl)-1,3-dihydro-5-isobenzofurancarbonitrile is reacted with 3-(N,N-dimethylamino)propyl-chloride in the presence of methylsulfinylmethide as condensing agent. The starting material was prepared from the corresponding 5-bromo derivative by reaction with cuprous cyanide.

According to the method, which is only outlined in general terms, citalopram may be obtained by ring closure of the compound:

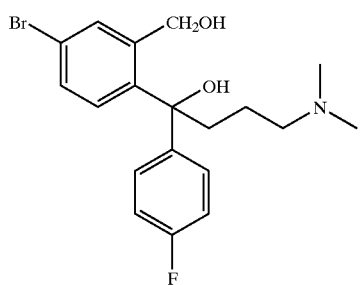

Formula II in the presence of a dehydrating agent and subsequent exchange of the 5-bromo group with cuprous cyanide. The starting material of Formula II is obtained from 5-bromophthalide by two successive Grignard reactions, i.e. with 4-fluorophenyl magnesium chloride and N,N-dimethylaminopropyl magnesium chloride, respectively.

A new and surprising method and an intermediate for the preparation of citalopram were described in U.S. Pat. No. 4,650,884, according to which an intermediate of the Formula

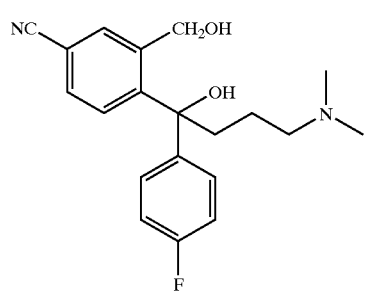

Formula III is subjected to a ring closure reaction by dehydration with strong sulfuric acid in order to obtain citalopram. The intermediate of Formula III was prepared from 5-cyanophthalide by two successive Grignard reactions, i.e. with 4-fluorophenyl magnesium halogenide and N,N-dimethylaminopropyl magnesium halogenide, respectively. Further processes are disclosed in international patent application Nos. WO 98019511, WO 98019512 and WO 98019513. WO 98019512 and WO 98019513 relate to methods wherein a 5-amino-, 5-alkoxycarbonyl- or 5-(sec. aminocarbonyl)phthalide is subjected to two successive Grignard reactions, ring closure and conversion of the resulting 1,3-dihydroisobenzofuran derivative to the corresponding 5-cyano compound, i.e. citalopram. International patent application No. WO 98019511 discloses a process for the manufacture of citalopram wherein a (4-substituted-2-hydroxymethylphenyl-(4-fluorophenyl)methanol compound is subjected to ring closure and the resulting 5-substituted 1-(4-fluorophenyl)-1,3-dihydroisobenzofuiran converted to the corresponding 5-cyano derivative,which is alkylated with a (3-dimethylamino)propylhalogenide in order to obtain citalopram. Finally, methods of preparing the individual enantiomers of citalopram are disclosed in U.S. Pat. No 4,943,590 from which it also appears that the ring closure of the intermediate of Formula HI may be carried out via a labile ester with a base.

It has now, surprisingly, been found that citalopram may be manufactured by a novel favourable and safe procedure using convenient starting materials.

SUMMARY OF THE INVENTION

Accordingly, the present invention relates to a novel method for the preparation of citalopram having the Formula I Formula I

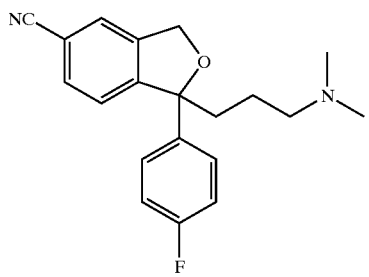

comprising:
reacting 5-carboxyphthalide successively with a Grignard reagent of 4-halo-fluorophenyl and a Grignard reagent of 3-halo-N,N-dimethyl-propylamine and then effecting ring closure of the resulting compound of Formula XI Formula XI

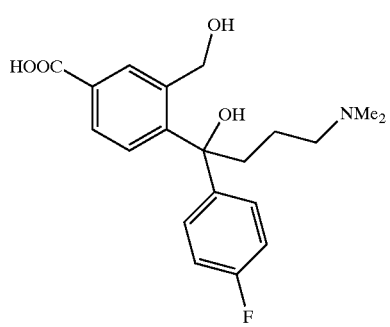

to a compound of Formula IV

Formula IV

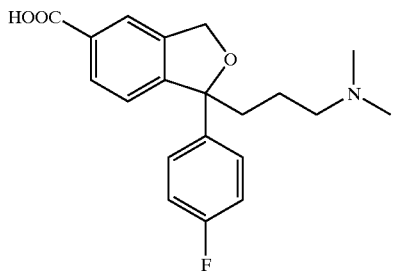

followed by conversion of the compound of Formula IV into citalopram.

In particular, the invention relates to such a method comprising:
i) reaction of the compound of Formula IV with a dehydrating agent and a sulfonamide of the Formula $H_2N—SO_2—R$ wherein R is:
  a) An optionally substituted $NH_2$, or $C_{1-6}$ alkyloxy,
  b) aryloxy or heteroaryloxy optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino, or
  c) aryl or heteroaryl optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino;
or ii) conversion of the compound of Formula IV to the corresponding amide of Formula V Formula V

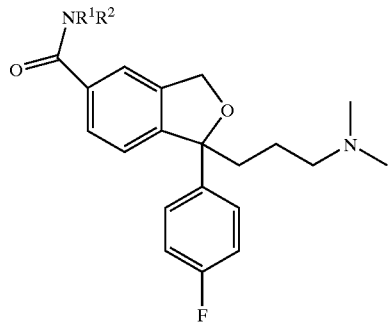

in which $R^1$ and $R^2$ are independently hydrogen, $C_{1-6}$ alkyl, $C_{1-6}$ alkyl substituted with one or more substituents selected from the group comprising aryl and heteroaryl, hydroxy, $C_{1-6}$-alkoxy, aryloxy, heteroaryloxy, aryl-$C_{1-6}$-alkoxy, or trisubstituted silyl wherein the substituents are independently $C_{1-6}$ alkyl, aryl, heteroaryl or aryl-$C_{1-6}$-alkyl and then reacting the amide of Formula V with a dehydrating agent thereby obtaining citalopram as the base or a pharmaceutically acceptable salt thereof The conversion of the 5-carboxy derivative of Formula IV to the amide of Formula V may be carried out via an activated acid derivative of Formula VI:

Formula VI

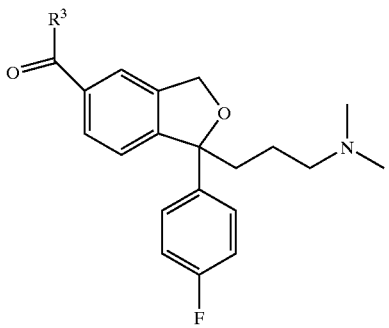

wherein $R^3$ is halogen, $C_{1-6}$alkoxy, aryloxy, heteroaryloxy, aryl-$C_{1-6}$-alkoxy, heteroaryl-$C_{1-6}$-alkoxy, alkylcarbonate, arylcarbonate, alkylcarbamate, arylcarbamate, alkylthiocarbonate, arylthiocarbonate, alkylthiocarbamate, arylthiocarbamate, alkylacyloxy, arylacyloxy, heteroarylacyloxy substituted or unsubstituted aryl or substituted or unsubstituted heteroaryl.

In another aspect, the invention relates to methods for the preparation of the intermediate of Formula IV comprising reaction of 5-carboxyphthalide successively with a Grignard reagent of 4-halo-fluorophenyl and a Grignard reagent of 3-halo-N,N-dimethyl-propylamine and then effecting ring closure of the resulting compound of Formula XI Formula XI

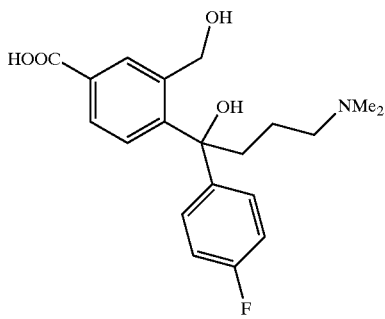

to a compound of Formula IV

The Grignard reagent of 4-halogen-fluorophenyl is a magnesium halide, such as the chloride, bromide or iodide. Preferably the magnesium bromide is used. The Grignard reagent of 3-halogen-N,N-dimethylpropylamine is a magnesium halide, such as the chloride, bromide or iodide, preferably the magnesium chloride. Preferably, the two reactions are performed successively without isolation of the intermediate resulting from the first Grignard reaction.

The ring closure of the compound of Formula XI is effected by an acid or via a labile ester with or without a base. Acidic ring closure is performed by an inorganic acid, such as a sulfuric or phosphoric acid, or an organic acid, such as methylsulfonic, p-toluenesulfonic or trifluoroacetic acid. The basic ring closure is performed via a labile ester, such as the methane sulfonyl, p-toluene sulfonyl, b 10-camphorsulfonyl, trifluoroacetyl or trifluoromethanesulfonyl ester with addition of a base, such as triethyl amine, dimethylaniline, pyridine, etc. The reaction is performed in an inert solvent, preferably with cooling, in particular about 0° C., and is preferably carried out by a one-pot procedure, i.e. with esterification and simultaneous addition of the base.

The 5-carboxyphthalide used as a starting material may be obtained by the methods described in U.S. Pat. No. 3,607,884 or German patent No. 2630927, i.e. by reacting a concentrated solution of terephthalic acid with formaldehyde in liquid S03 or by electrochemical hydrogenation of trimellithic acid.

In yet another aspect, the invention relates to a method for the preparation of citalopram Formula I

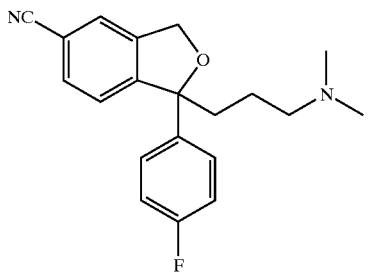

comprising reacting a compound of Formula IV

Formula IV

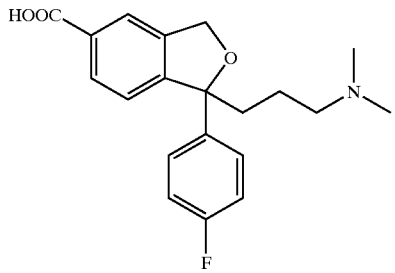

with a dehydrating agent and a sulfonamide of the formula $H_2N-SO_2-R$ wherein R is
  a) An optionally substituted $NH_2$, or $C_{1-6}$- alkyloxy,
  b) aryloxy or heteroaryloxy optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino, or
  c) aryl or heteroaryl optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino.

In yet another aspect, the present invention relates to an antidepressant pharmaceutical composition comprising citalopram as the base or any convenient salt thereof manufactured by the process of the invention.

Throughout the specification and claims, the term 'dehydrating agent' refers to any suitable dehydrating agent and a person skilled in the art may easily determine the optimal agent. Examples of suitable dehydrating agents are $SOCl_2$, $POCl_3$, $PCl_5$, $SOBr_2$, $POBr_3$, $PBr_5$, $SOI_2$, $POI_3$, $PI_5$, $P_4O_{10}$, oxalylchloride, carbonyldiimidazole and Vilsmeier reagents. Preferably a chloro-containing agent, most preferably $SOCl_2$ or $POCl_3$, is used. Vilsmeier reagents are reagents formed by mixing of N,N-dimethylformamide (DMF) and dehydrating agents, examples of which are $DMF/SOCl_2$ and $DMF/POCl_3$.

Throughout the specification and claims, $C_{1-6}$ alkyl refers to a branched or unbranched alkyl group having from one to six carbon atoms inclusive, such as methyl, ethyl, 1-propyl, 2-pro-pyl, 1-butyl, 2-butyl, 2-methyl-2-propyl, 2,2-dimethyl-1-ethyl and 2-methyl-1-propyl. Similarly, $C_{1-4}$alkyl refers to such a group having from one to four carbon atoms inclusive and $C_{1-6}$- alkoxy, $C_{1-4}$ alkoxy and $C_{1-4}$ alkylamine designate such groups wherein the alkyl moity is as defined.

Halogen means fluorine, chlorine, bromine or iodine.

In method i) of the invention, one possible but non-limiting mechanism of the reaction is that the 5-carboxy compound of Formula IV reacts with the dehydration agent in order to form a corresponding activated derivative, which then reacts with the sulfonamide, $H_2N-SO_2-R$, thereby forming citalopram. During the latter reaction, a catalytic amount of an acid may be necessary.

The sulfonamide, $H_2N-SO_2-R$, used in the process is preferably sulfamide, $NH_2-SO_2-NH_2$.

The optionally substituted $NH_2$ used in the process is preferably tert-butylamine.

The reactions with dehydration agents in the method of the invention are carried out neat or in a suitable solvent, such as sulfolane or acetonitrile. When a solvent is used in the dehydration reaction of ii), a catalytic amount of N,N-dimethylformamide may be needed.

In one embodiment of the invention, the manufacture of the compound of Formula IV and the conversion of the compound of Formula IV into citalopram is performed without isolation of the compound of Formula IV, a so called 'one-pot synthesis'.

In another embodiment of the invention, the compound of Formula IV is at least partially isolated before conversion to citalopram.

The compound of Formula I may be used as the free base or as a pharmaceutically acceptable acid addition salt thereof. As acid addition salts, such salts formed with organic or inorganic acids may be used. Exemplary of such organic salts are those with maleic, fumaric, benzoic, ascorbic, succinic, oxalic, bismethylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids. The acid addition salts of the compounds may be prepared by methods known in the art. The base is reacted with either the calculated amount of acid in a water miscible solvent, such as acetone or ethanol, with subsequent isolation of the salt by concentration and cooling, or with an excess of the acid in a water immiscible solvent, such as diethylether, ethylacetate or dichloromethane, with the salt separating spontaneously.

The pharmaceutical compositions of the invention may be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvant or additive colourings, aroma, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

EXAMPLES

The invention is further illustrated by the following examples, which should not be construed as limiting the scope of the invention.

EXAMPLE 1

5-Carboxy Citalopram

To a stirred suspension/solution of 5-carboxyphthalide (1.0 g, 5.7 mmol) in dry THF (20 mL) under a nitrogen atmosphere was added N,N,N N'-tetramethylethylenediamine (2.2 mL, 1.7 g, 14 mmol). A solution of p-fluorophenylmagnesium bromide (approx. 0.5 M) and magnesium bromide (approx. 0.125 M) in THF (approx. 60 mL) was added dropwise until no 5-carboxyphthalide remained. A solution of 3-(N,N-dimethylamino)propylmagnesium chloride in THF/heptane (approx. 2 M, approx 15 mL) was then added dropwise until none of the previous intermediate remained. The solution was then evaporated to give a crunchy solid. This solid was treated with saturated aqueous ammonium chloride solution (2 mL) and water (20 mL), and the pH was adjusted to pH 6 with aqueous hydrochloric acid solution (10 M). The solution was washed with ether. HPLC analysis of the aqueous layer indicated that the diol was present in sufficient purity to continue (>90% purity, HPLC peak area—UV 220 nm). The pH was adjusted to pH <−1 with aqueous hydrochloric acid solution (10 M) and the solution was stirred for 2 h. HPLC analysis indicated that the 5-carboxy citalopram was present in sufficient purity for further use (>80% purity, HPLC peak area—UV 220 nm).

EXAMPLE 2

5-Cyano--(4-fluorophenyl )-1-(3-dimethylaminopropyl)- 1,3-dihydro-isobenzofuiran. (Citalopram, Free Base)

5-Carboxy--(4-fluorophenyl)-1-(3-dimethylaminopropyl)- ,3-dihydro-isobenzofuran (5 g, 0.015 mole) and sulfamide (1.65 g, 0.017 mole) were dissolved in sulfolane (15 mL). Thionylchloride (2.25 g, 0.019 mole) was added at room temperature and the temperature of the reaction mixture was raised to 130° C. for 2 hours. The reaction mixture was allowed to Cool to 75° C. and water (25 mL) was added. The temperature was held at 75° C. for 15 min, and then the reaction mixture was cooled to room temperature. pH was ajusted to 9 with ammonium hydroxide and then n-heptane (75 mL) was added. The temperature was raised to 70° C. and the hot n-heptane layer was isolated, from which the title compound crystallised on cooling. Yield 3.77 g. Purity (HPLC peak area) >97%.

EXAMPLE 3

5-Cyano- 1-(4-fluorophenyl)- 1-(3-dimethylaminopropyl)- 1,3-dihydro-isobenzofuran Oxalate. (Citalopram, Oxalate)

To a stirred solution/suspension of 5-carboxyphthalide (57 mmol) and N,N,N',N'-tetramethylethylenediamine (144 mmol) in THF (200 mL) was added a solution of p-fluorophenylmagnesium bromide (approx. 0.5 M) and magnesium bromide (approx 0.125 M) in THF dropwise until no more starting phthalide remained. A solution of 3-(N,N-dimethylamino)propylmagnesium chloride (approx. 2 M in THF/heptane) was added dropwise until no more of the previous intermediate remained. Methanesulfonyl chloride (228 mmol) was added dropwise over 5 minutes in an exothermic reaction . After 30 min, DMF (5 mL) was added, followed by $POCl_3$ (228 mmol) dropwise over 10 minutes in a mildly exothermic reaction and the mixture was stirred for 2 h. t-Butylamine (285 mmol) was added dropwise over 15 minutes and the mixture was stirred overnight. DMF (5 mL) was added dropwise, followed by $POCl_3$ (2.3 mol) over 1 h. The mixture was stirred overnight, and was then heated to reflux for 1 h. The mixture was cooled in and ice/water bath, and water (200 mL) was cautiously added dropwise over 1 h in an exothermic reaction. The mixture was basified to pH >9 with an aqueous solution of ammonia in water (25% w/v). Toluene (100 mL) was added, and the mixture was filtered. The residue was washed with further toluene, the combined filtrates were separated, and the organic phase was collected. The organic phase was extracted twice with an aqueous solution of $H_2SO_4$ (10 % v/v). The combined acid extracts were basified to pH >9 with an aqueous solution of ammonia in water (25% w/v) and were extracted with toluene. The combined toluene layers were dried and evaporated to give citalopram base as a dark oil. The oxalate salt was prepared using standard procedures to give citalopram oxalate. Yield 9.2 g. Purity (HPLC peak area) >90%.

What is claimed is:

1. A method for the preparation of citalopram

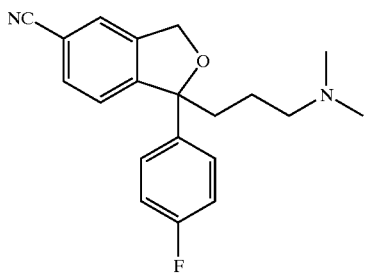

Formula I comprising reacting 5-carboxyphthalide successively with a Grignard reagent of 4-halo-fluorophenyl and a Grignard reagent of 3-halo-N,N-dimethyl-propylamine and then effecting ring closure of the resulting compound of Formula XI

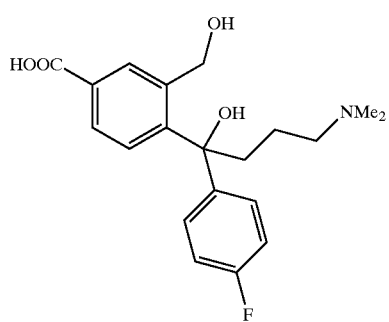

Formula XI to a compound of Formula IV

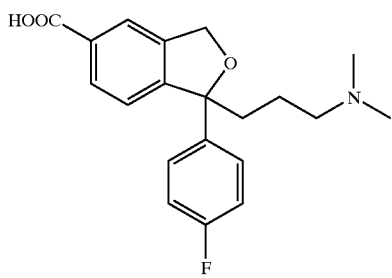

Formula IV followed by conversion of the compound of Formula IV into citalopram.

2. A method according to claim 1, wherein:

i) the compound of Formula IV is reacted with a dehydrating agent and a sulfonamide of the formula $H_2N$—$SO_2$—R wherein R is a) an optionally substituted NH2, or $C_{1-6}$ alkyloxy, b) aryloxy or heteroaryloxy optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino, or c) aryl or heteroaryl optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino; or ii) the compound of Formula IV is converted to the corresponding amide of Formula V

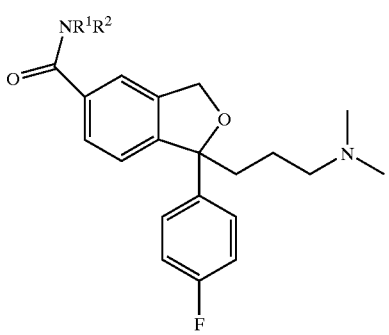

Formula V in which $R^1$ and $R^2$ are independently hydrogen, $C_{1-6}$ alkyl, $C_{1-6}$ alkyl substituted with one or more substituents selected from the group consisting of aryl and heteroaryl, hydroxy, $C_{1-6}$-alkoxy, aryloxy, heteroaryloxy, aryl-$C_{1-6}$-alkoxy, or trisubstituted silyl wherein the substituents are independently $C_{1-6}$ alkyl, aryl, heteroaryl or aryl-$C_{1-6}$-alkyl and then reacting the amide of Formula V with a dehydrating agent;

thereby obtaining citalopram as the base or a pharmaceutically acceptable salt thereof.

3. The method according to claim 2, wherein the compound of Formula IV is reacted with $SOCl_2$ and sulfamide.

4. The method of claim 3, wherein the reaction is performed in sulfolan.

5. The method according to claim 2, wherein the compound of Formula IV is reacted with $POCl_3$ and tert-butylamine.

6. The method of claim 1, wherein the manufacture of the compound of Formula IV and the conversion of the compound of Formula IV is performed without isolation of the compound of Formula IV.

7. The method of claim 1, wherein the compound of Formula IV is at least partially isolated before conversion to citalopram.

8. A method for the preparation of citalopram

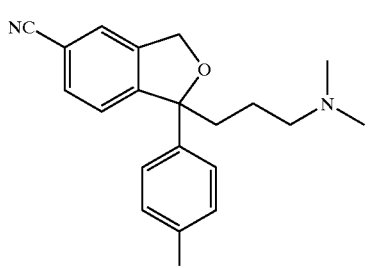

Formula I comprising reacting a compound of Formula IV

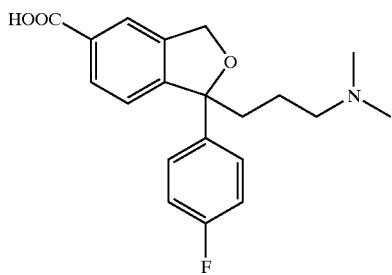

Formula IV with a dehydrating agent and a sulfonamide of the formula $H_2N\text{---}SO_2\text{---}R$ wherein R is
  d) an optionally substituted NH2, or $C_{1-6}$ alkyloxy,
  e) aryloxy or heteroaryloxy optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino, or
  f) aryl or heteroaryl optionally substituted with halogen, $C_{1-4}$-alkyl, cyano, hydroxy, $C_{1-4}$-alkoxy, trifluoromethyl, nitro, amino, $C_{1-4}$-alkylamino or di-$C_{1-4}$-alkylamino.

9. A method for the preparation of a compound of Formula IV, wherein the compound of Formula IV is obtained by reaction of 5-carboxyphthalide successively with a Grignard reagent of 4-halo-fluorophenyl and a Grignard reagent of 3-halo-N,N-dimethyl-propylamine and then effecting ring closure of the resulting compound of Formula XI.

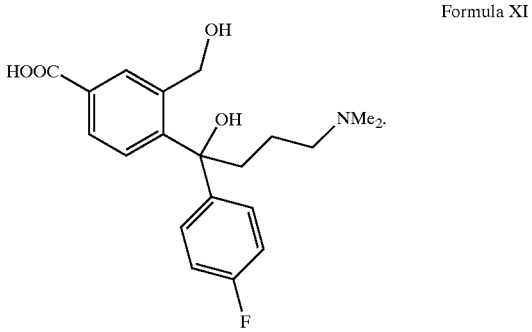

Formula XI

* * * * *